United States Patent [19]
Kim et al.

[11] Patent Number: 5,548,035
[45] Date of Patent: Aug. 20, 1996

[54] BIODEGRADABLE COPOLYMER AS DRUG DELIVERY MATRIX COMPRISING POLYETHYLENEOXIDE AND ALIPHATIC POLYESTER BLOCKS

[75] Inventors: Ho H. Kim; Guw D. Yeo, both of Tae Jeon; Yil W. Yi, Chon-Ju, all of Rep. of Korea

[73] Assignee: Sam Yang Co., Ltd., Seoul, Rep. of Korea

[21] Appl. No.: 238,083

[22] Filed: May 4, 1994

[30] Foreign Application Priority Data

Jan. 10, 1994 [KR] Rep. of Korea .................. 94-270

[51] Int. Cl.[6] .................................................. C08G 65/32
[52] U.S. Cl. .................. 525/408; 528/65; 528/66; 528/80; 528/81; 528/369; 560/157; 560/158; 560/166
[58] Field of Search .................. 525/408; 528/80, 528/65, 369, 66, 81; 560/157, 158, 166

[56] References Cited

U.S. PATENT DOCUMENTS

| | | | |
|---|---|---|---|
| 4,716,203 | 12/1987 | Casey et al. ............................. | 525/408 |
| 4,942,035 | 7/1990 | Churchill et al. ...................... | 424/423 |
| 4,963,638 | 10/1990 | Pezos et al. ............................. | 528/65 |

OTHER PUBLICATIONS

Journal of Polymer Science, Part A: Polymer Chemistry, vol. 27, 2151–2159 (1989): K. J. Zhu, et al.; *Super Microcapsules (SMC). Preparation and Characterization of Star Polyethylene Oxide (PEO) —Polylactide (PLA) Copolymers*.

Journal of Applied Polymer Science, vol. 39, 1–9 (1990), K. J. Zhu, et al.; *Preparation, Characterization, and Properties of Polylactide (PLA)—Poly(ethylene Glycol) (PEG) Copolymers: A Potential Drug Carrier*.

Journal of Applied Polymer Science, vol. 50, 1391–1396 (1993), David Shiaw–Guang Hu et al.: *Inhibition of Bovine Serum Albumin Adsoprtion by Poly(ethylene glycol) Soft Segment in Biodegradable Poly(ethylene glycol)/Poly(L--lactide) Copolymers*.

Journal of Applied Polymer Science, vol. 51, 473–482 (1994); David Shiaw–Guang Hu et al.; *Structural Analysis and Degradation Behavior in Polyethylene Glycol/Poly(L--Lactide) Copolymers*.

Primary Examiner—Frederick Krass
Attorney, Agent, or Firm—Kenyon & Kenyon

[57] ABSTRACT

This invention concerns the thermoplastic, biodegradable and nontoxic block copolymer which is easily degraded and excreted in human body by the hydrolysis of intramolecular ester and amide bond. The structure of present copolymer comprises i) hydrophilic and swellable soft domain consisting of polyethyleneoxide(PEO), and ii) hydrophobic, biodegradable, crystallizable and non-swellable hard domain consisting of polylactide(PLA), polyglycolide(PGA), polylactideglycolide(PLdA) and polycaprolactone(PCL).

8 Claims, No Drawings

BIODEGRADABLE COPOLYMER AS DRUG DELIVERY MATRIX COMPRISING POLYETHYLENEOXIDE AND ALIPHATIC POLYESTER BLOCKS

BACKGROUND OF THE INVENTION

1. Field of the Invention

The present invention relates to a novel thermoplastic, biodegradable multi block hydrogel copolymer used for drug delivery matrix, having hydrophobic both end blocks and hydrophilic middle block. More specifically, this invention concerns the thermoplastic, biodegradable hydrogels copolymer which is easily degraded and excreted in human body by the hydrolysis of intramolecular ester and amide bond. The structure of present copolymer comprises i) hydrophilic and swellable soft domain consisting of polyethyleneoxide(PEO), and ii) hydrophobic, biodegradable, crystallizable and non-swellable hard domain consisting of polylactide(PLA), polyglycolide(PGA), polylactideglycolide(PLGA) and polycaprolactone(PCL).

2. Description of the Prior Art

Recently, drug delivery system for regulating the drug release to the specific site within the range of constant effective dose has been researched very actively. For this purpose, biomedical polymers have been developed as drug delivery matrix. However, biomedical polymers developed so far have some drawbacks as follows:

i) It is hard to use biomedical polymers for delivering the drugs having large molecular weight;

ii) Physical treatment is required for removing the non-biodegradable copolymers, if non-biodegradable copolymers are used for drug delivery matrix; and iii) In case of hydrogels developed up to now, these materials have very low processibility due to their crosslinked nature. Furthermore, these materials cannot be used easily as drug delivery matrix for their toxicity to the human body.

To solve the above mentioned drawbacks, the inventors has researched thermoplastic, biodegradable copolymers having the following properties:

i) copolymers can be easily processed into appropriate preparations by simple processing methods, such as, infusion processing method or solvent casting method, since there is no chemical crosslinkage in copolymers; and ii) copolymers can be easily degraded into small and nontoxic moleculars by simple hydrolysis or enzyme hydrolysis in order to be easily excreted through kidney.

Biodegradable copolymers disclosed so far are aliphatic polyester, polyorthoester, polyanhydride, poly α-amino acid, polyphosphagen, polyalkylcyanoacrylate. Among the aliphatic polyesters, polylactide(PLA), polyglycolide (PGA) and polylactideglycolide (PLGA) have been approved as the nontoxic copolymers to human by the FDA. These copolymers have been applied as drug delivery devices to carry the drugs having small molecular weight.

Recently, polypetides or proteins produced by cell engineering or recombinant DNA technology have been approved as major medicines. However, these medicines have been administered only by injection, because these medicines are water-soluble and very unstable macromolecular compounds with short half-life. Therefore, finding another suitable delivery route of these compounds becomes a major research subject.

The application of aliphatic polyesters as delivery system of protein drugs has some handicaps owing to their difficulties in loading process, complicated release mechanism, low degradability and their hydrophobic property. Therefore, the improved degradable materials have been required as drug delivery matrix for protein drugs.

Block copolymers as drug delivery matrix were disclosed by U.S. Pat. No. 4,942,035. These copolymers are block copolymers in the shape of PLA/PEO/PLA or PGA/PEO/PGA which comprise polyethyleneoxide as hydrophilic block and polylactide(D-, L- or DL-form), polyglycolide, poly-ε-caprolactone or poly-3-hydroxybutylic acid as hydrophobic block. However, these block copolymers have some drawbacks as follows:

i) it is hard to be excreted from human body, and ii) the toxic materials like pentaerythrol are contained to these copolymers.

On the other hand, diblock and triblock copolymers having polyalkyleneoxide and trimethylene carbonate were disclosed by U.S. Pat. No. 4,716,203. These block copolymers were invented for coating materials, and contained some materials which are not easily degraded and toxic to human body.

Other block copolymers having polyethylene glycol as hydrophilic component and polylactide as hydrophobic component were reported in J. Pol. Sci. (A): Vol. 27,2151(1989) and J. Pol. Sci. (A): Vol. 39 (1990). However, these copolymers were prepared by simple copolymerization of the two components to be used as drug delivery matrix.

SUMMARY OF THE INVENTION

The object of the present invention is to provide a multiblock copolymer used for drug delivery matrix which has improved biodegradability and nontoxicity to the human body without having intramolecular crosslinkage.

Multi-block copolymers of the present invention used for drug delivery matrix are prepared by the synthesis of hydrophilic and swellable soft domain(A), and hydrophobic, biodegradable, crystallizable and non-swellable hard domain (B).

Multiblock coopolymers of the present invention can be shown as following formulas (I)a, (I)b, (I)c, (I)d and (I)e.

$$----Y-(X-)_n-Y----$$  Formula (I) a

Formula (I) b

Formula (I) c

Formula (I) d

Formula (I) e wherein

A(—) shows hydrophilic, non-biodegradable, and swellable polymers essentially consisting of polyethyleneoxide(PEO) and/or copolymer of PEO/polypropyleneoxide (PPO);

B(—) shows hydrophobic, biodegradable, crystallizable, and non-swellable polymers essentially consisting of polylactide(PLA), polyglycol ide (PGA), copolymer of PLA/PGA, polycaprolactone, polyorthoester and/or polyanhydride;

X shows the biodegradable chemical 1 inkage, such as, amide linkage, ester linkage, carbamate linkage and carbonate linkage;

Y shows the chemical linkage to link between block (A) and block (B), or block (B) and block (B), such as, amide linkage, ester linkage, carbamate linkage and carbonate linkage;

n shows the integer 0 to 20.

DETAILED DESCRIPTION OF THE INVENTION

As hydrophilic, non-biodegradable polymers, polyethyleneoxide and/or copolymer of PEO/PPO of M.W. 600–30,000, preferably 2,000–10,000, can be used. The polymers less than M.W. 2,000 show low flexibility and processiblility, and the polymers more than M.W. 10,000 are hard to be excreted through kidney.

To synthesize the PEO multi-block linked by biodegradable chemical linkage(X), polyethylene glycol (PEG) derivatives substituted by various functional groups are used, for example, HO—($CH_2CH_2O$)$_n$—H, $O_2NC_6H_4OCO$—O—($CH_2CH_2O$)$_n$—$CO_2C_6H_4NO_2$, $HO_2CCH_2CH_2O$—($CH_2CH_2O$)$_n$—$CH_2CH_2CO_2H$, $HO_2CCH_2O$—($CH_2CH_2O$)$_n$—$CH_2CO_2H$, HO—($CH_2CH_2O$)$_n$—$CH_2CO_2H$, HO—($CH_2CH_2O$)$_n$—$CONHCH_2CO_2H$, $H_2N$—($CH_2CH_2O$)$_n$H, $H_2NNHCOCH_2$—($CH_2CH_2O$)$_n$—H, and $H_2NCH_2COO$—($CH_2CH_2O$)$_n$—H. By coupling the above PEG derivatives, the biodegradable PEO multi-block is synthesized.

As hydrophobic, biodegradable, crystallizable and non-swellable polymers, polylactide(PLA), polyglycolide (PGA), polycaprolactone(PCL), and/or their copolymers can be used. Copolymers having various number of branches can be obtained by the chemical linkage(Y) between block(A) and block(B).

The preferred type of block copolymers of the present invention can be shown as following formula (I) and (I')

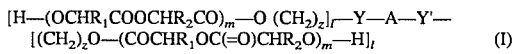

[H—(OCHR$_1$COOCHR$_2$CO)$_m$—O (CH$_2$)$_z$]$_l$—Y—A—Y'—[(CH$_2$)$_z$O—(COCHR$_1$OC(=O)CHR$_2$O)$_m$—H]$_l$     (I)

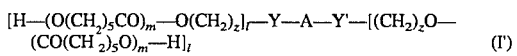

[H—(O(CH$_2$)$_5$CO)$_m$—O(CH$_2$)$_z$]$_l$—Y—A—Y'—[(CH$_2$)$_z$O—(CO(CH$_2$)$_5$O)$_m$—H]$_l$     (I')

wherein

A shows hydrophilic multi-block copolymer as—[—(OCH$_2$CH$_2$)$_n$—X]$_k$—(CH$_2$CH$_2$O)$_n$—;

X shows —O(CO CH$_2$O)$_x$—, —O [COCH(CH$_3$)O ]$_x$—, —OCH$_2$CONH—, —OCH$_2$CH$_2$CONH—, or —OCONH—;

Y shows —CHyNHCO—;

Y' shows —CONHCHy—;

R$_1$ and R$_2$ shows each independently hydrogen or methyl;

x shows the integer 1 to 10;

z shows the integer 1 to 5;

y shows tile integer 0, 1 or 2;

l shows the integer 1, 2 or 3;

m shows the integer 20 to 500;

n shows the integer 20 to 500; and k shows the integer 0 to 50. The weight of the PEO block lies between five (5) and ninety five (95) percent (w/w) of the multiblock copolymer.

The preparation method of multi-block copolymers of the present invention can be explained as follows.

1 Eq. of carboxymethyl polyethylene glycol [HO$_2$CCH$_2$O(CH$_2$CH$_2$O)$_n$—CH$_2$CO$_2$H] of M.W. 600–30,000, 2 Eq. of polyethylene glycol (PEG) of M.W. 600–30,000 and 2 Eq. of dicyclohexanediamine are laid on well dried reactor, and reacted in the presence of proper organic solvent. After filtration, filtered material is precipitated in non-polar solvent. Finally, hydrophilic multi-block copolymer(A) having ester linkage(X) is obtained.

1 Eq. of PEG of M.W. 600–30,000 and 2.5 Eq. of P-nitrophenylchloroformate(NPC) or carbonyl di imidazole(CDI) are dissolved in organic solvent, and 2.5 Eq. of base, such as, triethylamine or pyridine is added and reacted. Reacted material is filtered arid added to non-polar solvent. Polyethylene glycol, both ends hydroxyl groups of which are protected by NPC, (NPC-PEG-NPC) is precipitated. 1 Eq. of dried NPC-PEG-NPC and 2 Eq. of α-amino-ω-hydroxy polyethylene glycol (H$_2$N-PEG-OH) are reacted and filtered. After precipitating in non-polar solvent, hydrophilic multi-block copolymer(A) having carbamate linkage(X) is obtained.

The same process described above is repeated, using the PEG derivatives, both ends hydroxyl groups of which are replaced by various functional groups. The hydrophilic multi-block copolymers (A) having various biodegradable linkages, such as, amide, ester, carbonate and/or carbamate linkage are obtained.

Both ends hydroxyl groups of hydrophilic multi-block copolymers obtained above are activated by p-nitrophenylchloroformate(NPC) or carbonyl diimidazole(CDI). After activation, obtained copolymer is reacted with tris (hydroxyalkyl)aminomethane in polar solvent, and reacted material is precipitated in non-polar solvent. Three(3) hydroxyl groups in both ends of polymer are introduced, which can be detected by NMR proton peaks (3.22 ppm).

1 Eq. of PEO multi-block copolymer having both ends hydroxyl groups obtained above is laid on well-dried reactor, and dissolved in THF solvent. And, 0.05–0.5N of potassium-naphthalene solution is added to tile reactor. When the potassium-naphthalene solution is added in the same equivalent amount of hydroxyl groups of the copolymer, the color of the solution disappears from pale green.

At the same time of color disappearance, a required amount of glycolide or lactide, monomer of hydrophobic block, is added and polymerized. Finally, the biodegradable hydrogel copolymer of the present invention is obtained.

As described above, the multi-block copolymer of the present invention comprises i) hydrophilic middle block which is linked by biodegradable linkage among PEOs or copolymers of PEO/PPO, and ii) hydrophobic both end blocks comprise PLA, PGA, PGLA, PCL and/or their copolymers.

By changing the M.W. or components of each block, various type of thermoplastic, biodegradable hydrogel copolymers can be prepared. Therefore, various copolymers can be easily synthesized according to the present invention.

The present invention can be explained more specifically by following examples, but it is not limited by following examples.

EXAMPLE 1

1 mmole of polyethylene glycol(PEG) of M.W. 3,400, 2.5 mmole of p-nitrophenylchloroformate(NPC), 200 ml of THF and 2.5 mmole of pyridine were laid on well-dried reactor, and stirred for 24 hours. After filtration, filtered material was precipitated in ether. Polyethylene glycol, both ends hydroxyl groups of which are protected by NPC, (NPC-PEG-NPC) was obtained.

1 mmole of dried NPC-PEG-NPC and 2 mmole of α-amino-ω-hydroxy polyethylene glycol (H$_2$N-PEG-OH) were laid on well-dried reactor, and reacted for 48 hours. Finally, triblock PEO was obtained. The yield of transformation detected by GPC is 79.2%.

1 mmole of triblock PEO obtained above, 3 mmole of NPC and THF or DMSO as solvent were mixed, and 3 mmole of pyridine as base was added with stirring. After stirring for 24 hours at room temperature, the reacted material was filtered, and precipitated in ether. Triblock PEO, both ends of hydroxyl groups of which are protected by NPC, (NPC-PEO-PEO-PEO-NPC) was obtained.

0.1 mmole of dried NPC-multiblock PEO, 0.2 mmole of tris(hydroxymethyl) aminomethane and DMSO as solvent were mixed and reacted for 24 hours. Reacted material was precipitated in ether, and obtained polymer was washed by excessive water to remove the unreacted tris(hydroxymethyl) aminomethane.

The obtained copolymer showed proton peak of hydroxyl group at 3.22 ppm by NMR(DMSO-d$_6$) analysis. And, the amount of hydroxyl end group measured by neutralization method showed 4.8–5.2 mEq./g, and M.W. of obtained copolymer was 10,600.

EXAMPLE 2

The Tris-multiblock PEO was obtained as the same process of example 1 except that 1 mmole of PEG of M.W. 2,000 and 2 mmole of α-amino-ω-hydroxy polyethylene glycol (H$_2$N-PEG-OH) were used. The obtained copolymer showed proton peak of hydroxyl group at 3.22 ppm by NMR analysis, and the amount of hydroxyl end group showed 5.0–5.5 mEq./g. (M.W.=6,500)

EXAMPLE 3

The Tris-multiblock PEO was obtained as the same process of example 1 except that 1 mmole of PEG of M.W. 3,000 and 2 mmole of α-amino-ω-hydroxy polyethylene glycol (H$_2$N-PEG-OH) were used. The obtained copolymer showed proton peak of hydroxyl group at 3.22 ppm by NMR analysis, and the amount of hydroxyl end group showed 5.0–5.5 mEq./g. (M.W.=9,500)

EXAMPLE 4

The Tris-multiblock PEO was obtained as the same process of example 1 except that 1 mmole of PEG of M.W. 5,000 and 2 mmole of α-amino-ω-hydroxy polyethylene glycol (H$_2$N-PEG-OH) were used. The obtained copolymer showed proton peak of hydroxyl group at 3.22 ppm by NMR analysis, and the amount of hydroxyl end group showed 4.0–4.5 mEq./g. (M.W.=15,600)

EXAMPLE 5

0.1 mmole of Tris-multiblock PEO(M.W.=10,600) obtained in example 1 was laid on well-dried reactor, and dissolved in THF solvent. And, 0.6 mmole of 0.1N-potassium naphthalene solution was added. When the color of the solution disappeared from pale green, L-lactide as same weight of Tris-multiblock PEO was added. After reaction for 30 minutes, small quantity of acetic acid dissolved in ether was added for finishing the reaction. After precipitating in cool methanol, the precipitated material was laid in a refrigerator for one day, and obtained material was filtered and dried in vacuum.

The composition of above obtained copolymer showed Tris-multiblock PEO: PLA=1:1.06. The proton peaks of lactide in NMR showed at 5.16 and 1.56 ppm, and the proton peak of oxyethylene(—CH$_2$CH$_2$O—) showed at 3.64 ppm. Number average molecular weight was 22,000.

EXAMPLE 6

The copolymer was obtained as the same process of example 5 except that Tris-multiblock PEO obtained in example 2(M.W.=6,500) and L-lactide were used in weight ratio(1:1.7). Number average molecular weight of obtained copolymer was 18,000.

EXAMPLE 7

The copolymer was obtained as the same process of example 5 except that Tris-multiblock PEO obtained in example 3(M.W.=9,500) and L-lactide were used in weight ratio(1:1.2). Number average molecular weight of obtained copolymer was 22,000.

EXAMPLE 8

The copolymer was obtained as the same process of example 5 except that Tris-multiblock PEO obtained in example 4(M.W.=15,600) and L-lactide were used in weight ratio(1:0.7). Number average molecular weight of obtained copolymer was 17,000.

EXAMPLE 9

3 mmole of polyethylene glycol (PEG) of M.W. 3,400, 1.5 mmole of α, ω-carboxy methyl PEG [HO$_2$CCH$_2$O(CH$_2$CH$_2$O)$_n$—CH$_2$CO$_2$H] and THF as solvent were laid on well-dried reactor, and stirred for 24 hours at room temperature. After filtration, filtered material was precipitated in ether. Triblock PEO linked by ester linkage was obtained.

1 mmole of dried triblock PEO, 2 mmole of p-nitrophenyl chloroformate (NPC), 2 mmole of pyridine and THF as solvent were mixed and stirred for 48 hours. Reacted material was filtered, and precipitated in ether. Triblock PEO, both ends of hydroxyl groups of which are protected by NPC, (NPC-PEO-PEO-PEO-NPC) was obtained.

0.1 mmole of dried NPC-multiblock PEO, 0.2 mmole of tris(hydroxymethyl) aminomethane and DMSO as solvent were mixed and reacted for 24 hours. Reaction mixture was precipitated in ether, and obtained polymer was washed by excess water to remove the unreacted tris(hydroxymethyl) aminomethane.

The obtained copolymer showed proton peak of hydroxyl group at 3.22 ppm and proton peak of —OCH$_2$C— at 5.19 ppm by NMR(DMSO-d$_6$) analysis. And, the amount of hydroxyl end group measured by neutralization method showed 4.7–5.0 mEq./g, and M.W. of obtained copolymer was 10,500.

EXAMPLE 10

The Tris-multiblock PEO was obtained as the same process of example 9 except that PEG of M.W. 2,000 and α, ω-carboxy methyl PEG of M.W. 2,000 were used. The obtained copolymer showed proton peak of hydroxyl group at 3.21 ppm and proton peak of —OCH$_2$C— at 5.20 ppm by NMR analysis, and the amount of hydroxyl end group showed 5.8–6.2 mEq./g. (M.W.=6,600)

EXAMPLE 11

The Tris-multiblock PEO was obtained as the same process of example 9 except that PEG of M.W. 3,000 and α, ω-carboxy methyl PEG of M.W. 3,000 were used. The obtained copolymer showed proton peak of hydroxyl group at 3.21 ppm and proton peak of —OCH$_2$C— at 5.21 ppm by NMR analysis, and the amount of hydroxyl end group showed 4.6–5.1 mEq./g. (M. W.=9,300)

EXAMPLE 12

The Tris-multiblock PEO was obtained as the same process of example 9 except that PEG of M.W. 5,000 and α, ω-carboxy methyl PEG of M.W. 5,000 were used. The obtained copolymer showed proton peak of hydroxyl group at 3.21 ppm and proton peak of —OCH$_2$C— at 5.21 ppm by NMR analysis, and the amount of hydroxyl end group showed 4.0–4.5 mEq./g. (M. W.=15,400)

EXAMPLE 13

0.1 mmole of Tris-multiblock PEO(M.W.=10,500) obtained in example 9 was laid on well-dried reactor, and dissolved in THF solvent. And, 0.6 mmole of 0.1N-potassium naphthalene solution was added. When the color of the solution disappeared from pale green, L-lactide as 1.5 times weight of Tris-multiblock PEO was added. After reaction for 30 minutes, small quantity of acetic acid dissolved in ether was added for finishing the reaction. After precipitating in cool methanol, the precipitated material was laid in a refrigerator for one day, and obtained material was filtered and dried in vacuum.

The composition of above obtained copolymer showed Tris-multiblock PEO:PLA=1:1.57. The proton peaks of lactide in NMR showed at 5.20 and 1.56 ppm, and the proton peak of oxyethylene(—CH$_2$CH$_2$O—) showed at 3.64 ppm. Number average molecular weight was 27,000.

EXAMPLE 14

The copolymer was obtained as the same process of example 13 except that Tris-multiblock PEO obtained in example 10(M.W.=6,600) and L-lactide were used in weight ratio(1:2.6). Number average molecular weight of obtained copolymer was 17,000.

EXAMPLE 15

The copolymer was obtained as the same process of example 13 except that Tris-multiblock PEO obtained in example 11(M.W.=9,300) and L-lactide were used in weight ratio(1:1.7). Number average molecular weight of obtained copolymer was 25,000.

EXAMPLE 16

The copolymer was obtained as the same process of example 13 except that Tris-multiblock PEO obtained in example 12(M.W.=15,400) and L-lactide were used in weight ratio(1:1). Number average molecular weight of obtained copolymer was 32,000.

We claim:
1. A thermoplastic, biodegradable multi-block copolymer useful as a drug delivery matrix with the following formula (I):

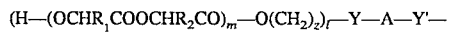

wherein
block A is a hydrophilic multi-block copolymer —(—(OCH$_2$CH$_2$)$_n$—X)$_k$—(CH$_2$CH$_2$O)$_n$—;
X is —O(COCH$_2$O)$_x$—, —O(COCH(CH$_3$)O)$_x$—, —OCH$_2$CONH—, —OCH$_2$CH$_2$CONH—, or —OCONH—;
Y is —CH$_z$NHCO—;
Y' is —CONHCH$_y$—;
R$_1$ and R$_2$ are each independently hydrogen or methyl;
x is an integer from 1 to 10;
z is an integer from 1 to 5;
y is an integer from 0 to 2;
l is an integer from 1 to 3;
m is an integer from 20 to 500;
n is an integer from 20 to 500; and
k is an integer from 0 to 50.

2. A thermoplastic, biodegradable multi-block copolymer useful as a drug delivery matrix with the following formula (I'):

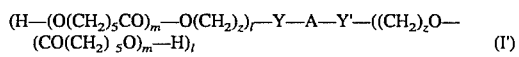

wherein
block A is a hydrophilic multi-block copolymer —(—(OCH$_2$CH$_2$)$_n$—X)$_k$—(CH$_2$CH$_2$O)$_n$—;
X is —O(COCH$_2$O)$_x$—, —O(COCH(CH$_3$)O)$_x$—, —OCH$_2$CONH—, —OCH$_2$CH$_2$CONH—, or —OCONH—;
Y is —CH$_z$NHCO—;
Y' is —CONHCH$_y$—;
R$_1$ and R$_2$ are each independently hydrogen or methyl;
x is an integer from 1 to 10;
z is an integer from 1 to 5;
y is an integer from 0 to 2;
l is an integer from 1 to 3;
m is an integer from 20 to 500;
n is an integer from 20 to 500; and
k is an integer from 0 to 50.

3. A thermoplastic, biodegradable multi-block copolymer useful as a drug delivery matrix according to claim 2, wherein the weight of block A ranges from five (5) percent (w/w) to ninety-five (95) percent (w/w) of said multi-block copolymer.

4. A thermoplastic, biodegradable multi-block copolymer useful as a drug delivery matrix according to claim 1, wherein the weight of block A ranges from five (5) percent (w/w) to ninety-five (95) percent (w/w) of said multi-block copolymer.

5. A thermoplastic, biodegradable multi-block copolymer according to claim 1, wherein the molecular weight of block A is in the range of from 600 to 30,000 D.

6. A thermoplastic, biodegradable multi-block copolymer according to claim 1, wherein the molecular weight of block A is in the range of from 2,000 to 10,000 D.

7. A thermoplastic, biodegradable multi-block copolymer according to claim 2, wherein the molecular weight of block A is in the range of from 600–30,000 D.

8. A thermoplastic, biodegradable multi-block copolymer according to claim 2, wherein the molecular weight of block A is in the range of from 2,000–10,000 D.

* * * * *